US 6,695,838 B2

(12) United States Patent
Wellman et al.

(10) Patent No.: US 6,695,838 B2
(45) Date of Patent: Feb. 24, 2004

(54) SYSTEM AND METHOD FOR PERFORMING CARDIAC TISSUE ABLATION

(75) Inventors: Parris S. Wellman, Hillsborough, NJ (US); Rajesh Pendekanti, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/966,765

(22) Filed: Sep. 28, 2001

(65) Prior Publication Data

US 2003/0065320 A1 Apr. 3, 2003

(51) Int. Cl.$^7$ .............................................. A61B 18/18
(52) U.S. Cl. .......................... 606/41; 128/898; 607/122
(58) Field of Search .............. 600/41–52; 607/101–102, 607/122; 128/898

(56) References Cited

U.S. PATENT DOCUMENTS

| | | | |
|---|---|---|---|
| 5,697,928 A | 12/1997 | Walcott et al. ................. 606/41 |
| 5,904,711 A | 5/1999 | Flom et al. .................. 607/129 |
| 6,012,457 A | 1/2000 | Lesh ........................... 128/898 |
| 6,079,414 A | 6/2000 | Roth ........................... 128/898 |
| 6,149,649 A | * 11/2000 | McGarry et al. .............. 606/45 |
| 6,161,543 A | 12/2000 | Cox et al. .................... 128/898 |
| 6,164,283 A | 12/2000 | Lesh ........................... 128/898 |
| 6,237,605 B1 | 5/2001 | Vaska et al. ................. 128/898 |
| 6,245,064 B1 | 6/2001 | Lesh et al. .................... 606/34 |
| 6,251,109 B1 | 6/2001 | Hassett et al. ................. 606/45 |
| 6,325,797 B1 | * 12/2001 | Stewart et al. ................. 606/41 |

OTHER PUBLICATIONS

Javier Roman–Gonzalez et al. "Collateral Tissue Injury Occuring During Intrapericardial Catheter Ablation in the Closed Chest Canine Model" North American Society for Pacing and Clinical Electrophysiology 22$^{nd}$ Annal Scientific Sessions, Hynes Convention Center, Boston, Masschusetts, UAS 388 (May 2–5, 2001).
David E. Haines et al. "Rapid, Continuous and Transmural Linear Ablation With a Novel Bipolar Radiofrequency Ablation System" North American Society for Pacing and Clinical Electrophysiology 22$^{nd}$ Annual Scientific Sessions, Hynes Convention Center, Boston, Masschusetts, USA 388 (May 2–5, 2001).

* cited by examiner

*Primary Examiner*—Linda C. M. Dvorak
*Assistant Examiner*—David M. Ruddy
(74) *Attorney, Agent, or Firm*—Nutter McClennen & Fish LLP

(57) ABSTRACT

A method of forming a lesion at a predetermined heart location is provided. An energy-delivering electrode is positioned proximal to the predetermined heart location; a return electrode is positioned in contact with cardiac tissue. An electrosurgical current, capable of delivering energy through the energy-delivering electrode to the predetermined heart location at a magnitude and for a duration effective to form a lesion is established. A system for treating atrial fibrillation by forming transmural lesions and a heart-positioning device including a return electrode are also provided.

17 Claims, 3 Drawing Sheets

SYSTEM AND METHOD FOR PERFORMING CARDIAC TISSUE ABLATION

CROSS REFERENCE TO RELATED APPLICATIONS

Not Applicable.

FIELD OF THE INVENTION

This application relates to systems and methods for ablating cardiac tissue. More particularly, it relates to systems and methods for the treatment of atrial fibrillation.

BACKGROUND OF THE INVENTION

Cardiac arrhythmias, such as atrial fibrillation, are commonly occurring disorders characterized by erratic beating of the heart. The regular pumping function of the atria is replaced by a disorganized, ineffective quivering caused by chaotic conduction of electrical signals through the upper chambers of the heart. Atrial fibrillation may be caused by the rapid and repetitive firing of an isolated center or focus within the atrial cardiac muscle tissue. Such foci may act to trigger AF or may, once triggered, sustain the fibrillation. Recent studies have suggested that foci for such arrhythmia are predominantly in a region of cardiac tissue proximal to the pulmonary veins that extend out of the heart from the left atrium. More particularly, tissue proximal to the superior pulmonary veins denoted as ostia are likely AF foci.

While medication can be an effective treatment for some cases, many patients are not responsive to medical therapies and require alternative treatment. As an alternative to medication, a surgical technique, known as the Maze technique, requires open chest surgery to strategically incise the atrial wall, and subsequently repair the incisions by suturing. The result of this surgery is to create scar tissue located along the incision lines and extending through the atrial wall to block electrical conductivity from one segment to another.

While the Maze procedure has proven effective in restoring normal sinus rhythm, it requires considerable prolongation of cardiopulmonary bypass and aortic crossclamp time, especially when performed in combination with other open heart procedures. Over the last decade, more simplified techniques have been proposed which replace surgical incisions with ablations, or scars, formed in the heart tissue. The various energy sources used in ablation technologies include cryogenic, radiofrequency (RF), laser, and microwave energy. The ablation devices are used to create tissue lesions in an affected portion of the heart in order to block electrical conduction.

One common ablation technique employs the use of a catheter that is introduced into the heart (e.g., intravascularly) to direct RF energy at specific areas of heart tissue found to be the source of the irregular rhythms. An electrophysiology (EP) study is first performed to discover the location and characteristics of the arrhythmia and, once the specific location is identified and mapped, RF energy is delivered to the tissue to ablate the tissue, thus forming a lesion that blocks electrical conduction. While minimally invasive techniques are usually preferred, the procedure is often performed in combination with other open heart procedures as a prophylactic to prevent post-operative onset of atrial fibrillation.

RF ablation techniques are typically successful in treating atrial fibrillation, however the lesions must be well defined within the heart to be effective. The lesion must have a sufficient length, continuity and/or depth to interrupt or to block electrical conduction across the affected portion of the heart. This can be difficult to achieve without forming an incision in the atrium.

In addition, if the energy is not uniformly transmitted to the target site, hot spots can form, possibly leading to severe tissue damage or blood coagulation (clots).

One potential problem that may be encountered during cardiac ablation procedures is the risk of collateral tissue damage. In some cases the energy-delivering electrode performing the ablation is positioned at the purported focus and a pad, which acts the return electrode, is externally placed on the patient's body. Although most of the generated energy may be appropriately directed at the focus, the uncertain, unpredictable energy return path from the heart to the return electrode pad may lead to damage of other vital organs or structures. The esophagus, the lungs, and nerve tissue are examples of organs or tissue structures that may be susceptible to unintended energy influx.

Accordingly, there exists a need for ablation systems and methods that can be used safely and effectively to effect cardiac ablation procedures.

SUMMARY OF THE INVENTION

The present invention provides ablation systems and methods for treating atrial fibrillation utilizing RF energy. The system comprises an energy delivering electrode and a return electrode that is placed in contact with tissue (e.g., cardiac tissue) within the patient's body. The use of such a system and method of the present invention is advantageous because it facilitates safe and effective ablation procedures in which the dispersion of current is controlled so as to minimize the potential for causing unintended collateral damage to non-target, sensitive tissue structures and organs.

According to a method of the invention, the return electrode is positioned in contact with tissue (e.g., cardiac tissue) within the patient's body. With the return electrode properly secured and placed to provide a controlled path for current, the energy-delivering electrode is positioned is proximal to a part of an organ (e.g., the heart) where it is desired to effect ablation. An electrosurgical current is then established through the target tissue, between the energy-delivery electrode and the return electrode. The current should be delivered at a magnitude and for a duration effective to form a lesion that is sufficient to block electrical conductivity at the focus or foci. Preferably, the lesion is transmural, extending through the wall of the heart at the target site from an endocardial surface to an epicardial surface thereof, and it is continuous along its length. In one embodiment, the return electrode has a surface area that is larger than a surface area of the energy-delivering electrode.

An electrosurgical generator is used with the method of the invention to deliver current to the target tissue. The generator can be one that is able to operate in the bipolar and/or monopolar modes.

In one aspect, the target tissue is a surface segment of a portion of the heart, such as the left atrium. More particularly, the target tissue may be adjacent to a pulmonary vein ostium. The invention provides sufficient flexibility that the energy delivering and return electrodes can be placed in contact with or adjacent to target tissue that is on either an epicardial or endocardial surface of the heart. Moreover, the method may be utilized by accessing the target tissue through a sternotomy, through a thoracoscopic portal, or by other techniques. The method may be performed upon a beating heart or upon a stopped heart.

The return electrode that is utilized with the invention may take a variety of forms. In one aspect, the return electrode is of a patch-like shape that is able to be affixed by various techniques to the appropriate tissue in the patient's body. Alternatively, the return electrode can be attached to or integral with another tool or device that is utilized by the surgeon and which is in intimate contact with the patient's tissue (e.g., the heart) during the surgical procedure. For example, the return electrode may be attached to or integral with a heart positioning or manipulation device that is used to spatially manipulate the heart during a surgical procedure.

The invention further contemplates systems and devices that facilitate the practice of the invention.

BRIEF DESCRIPTION OF THE DRAWINGS

The invention will be more fully understood from the following detailed description taken in conjunction with the accompanying drawings, in which.

DETAILED DESCRIPTION OF THE INVENTION

In one aspect, the invention provides a method and system useful to safely and effectively ablate tissue. The system includes energy-delivering and return electrodes that are designed and oriented to enable the current pathways to be more predictable, thus eliminating the risk of collateral damage to heat- and current-sensitive tissue structures and organs that may result from stray current pathways. For example, in the case of ablation of heart tissue, the present invention enables current to travel through cardiac tissue and between the electrodes, thus avoiding heat-current-sensitive tissue and organs such as the lungs and the esophagus. Although the invention is primarily described with respect to the ablation of cardiac tissue, one of ordinary skill in the art will recognize that the invention is also applicable to ablation procedures conducted on other organs and tissues.

Figure 1:
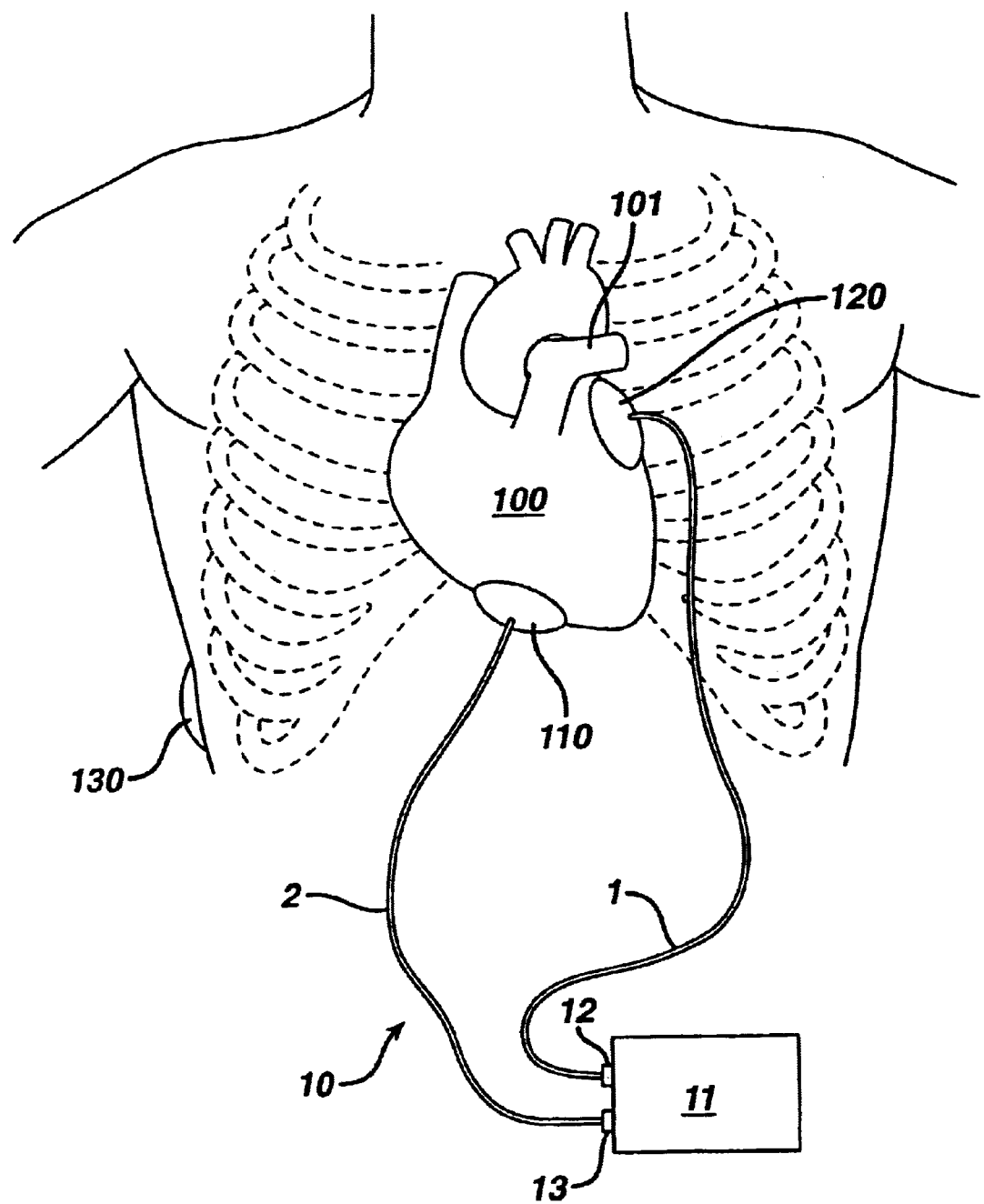
FIG. 1 is a schematic representation of a system according to one embodiment of the invention, useful to treat atrial fibrillation.

As shown in FIG. 1, system 10 is has an energy-delivering electrode 120 which communicates with one terminal 12 of an energy source 11 through conductor 1. The system 10 also includes a return electrode 110 that communicates with another terminal 13 of energy source 11 through conductor 2.

Energy delivering electrode 120 may take a variety of forms. Generally, virtually any type of conductive element can be used as the energy delivering electrode, provided that it is capable of accessing the desired target tissue (e.g., in the heart) and delivering electrosurgical current to a specific tissue location. The exact design of the energy-delivering electrode will vary depending on whether it is to be used in an open chest surgical procedure, a thoracosopic surgical procedure, or in another type of surgical approach.

Figure 2:
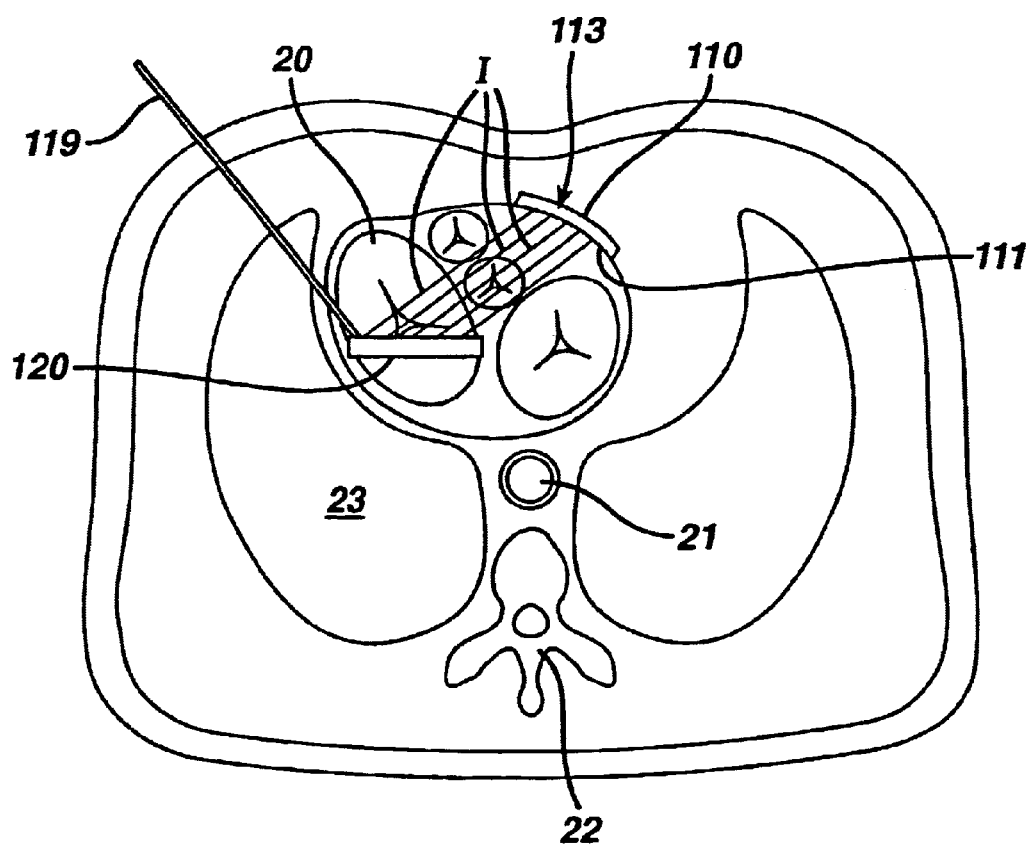
FIG. 2 is a cross-sectional view of the human body, in the axial plane, schematically illustrating one embodiment of the system of the invention.

FIG. 2 illustrates one embodiment of the energy-delivering electrode 120 that includes an elongate handle 119 having a conductive, electrode member 120 at its distal end. The handle 119 may be flexible or malleable. Further, the handle may be constructed such that the distal end of the handle and/or the electrode 120 can be selectively deflected by the surgeon. In one embodiment useful for an epicardial or endocardial ablation of cardiac tissue through an open chest procedure, the electrode 120 has a conductive surface area in the range of about 2 to 100 $mm^2$.

One having ordinary skill in the art will appreciate that minor modifications can be made to adapt the energy-delivering electrode 120 for ablation procedures conducted through thoracoscopic approaches or other minimally invasive surgical approaches. That is, the conductive element should be disposed at the distal end of an elongate element that is of a size and shape to enable it to be delivered to the surgical site through a thoracoscopic portal or through another access port. The elongate handle may be flexible or malleable to enable the energy-delivering electrode to be oriented and positioned in a desired manner. Alternatively or in addition, the distal end of the element that includes electrode 120 may be capable of selective articulation with respect to the elongate element. The surface area of the energy-delivering electrode useful in a thoracoscopic approach should be in the range of about 2 to 50 $mm^2$.

The energy-delivering electrode 120 can be made from a variety of suitable materials that are both conductive and biologically compatible. Examples of such materials include titanium, titanium alloys (including nickel-titanium alloys), and stainless steels.

Figure 3:
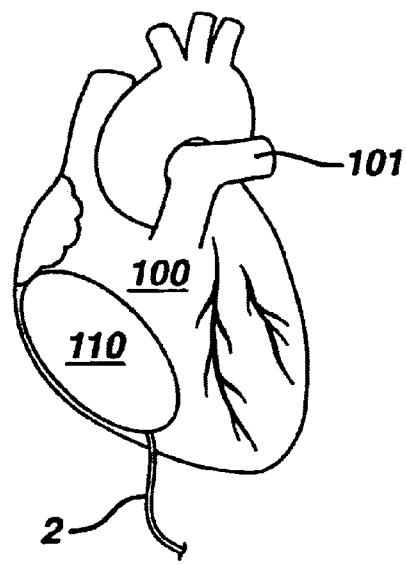
FIG. 3 is a plan view of a return electrode in contact with cardiac tissue according to one aspect of the invention.

In one embodiment the return electrode 110 may be a patch-like member as shown in FIGS. 1–3. The return electrode should have a conductive surface area that is greater than that of the energy-delivering electrode 120. Preferably, the tissue contacting conductive surface area of the return electrode should be about 10 to 100 times greater than the conductive surface area of the energy-delivering electrode. In one embodiment the return electrode 110 has a tissue contacting conductive surface area in the range of about 30 to 1000 $mm^2$.

As illustrated, the patch-like return electrode 110 car be a substantially planar member that is able to conform to and remain in contact with cardiac tissue within a patient's body cavity as shown in FIGS. 1–3. Alternatively, the patch-like return electrode can have a contoured surface that optimizes its ability to mate with a certain type of organ or tissue within a patient's body. The return electrode 110, or portions thereof, should be flexible and/or malleable to enable it to conform to the tissue against which it is placed. Although the return electrode 110 is shown to be in contact with tissue on the epicardial surface of the heart, it can be in contact with the endocardial surface of the heart, or other cardiac tissue such as the pericardium.

The return electrode 110 may have a conductive tissue contacting surface 111 and an opposed non-conductive surface 113 (FIG. 2). The non-conductive surface 113 can be formed from an insulator and/or a non-conductive material such as a biologically compatible polymer or fabric. Examples of such materials include expanded PTFE, polypropylene mesh, nylon, and polyester. The conductive surface 111 can be formed from a material that is both conductive and biologically compatible. The conductive material can be embedded within or otherwise affixed to the non-conductive surface 111. In another embodiment, the return electrode 110 is a conductive plate-like member that is covered on the surface 113 with a non-conductive material.

Examples of conductive materials from which the return electrode 110, or tissue contacting surface 111, can be made include a conductive composite material (e.g., conductive polyvinylidene fluoride or carbon loaded ultra-high molecular weight polyethylene), stainless steel, titanium, platinum, gold, silver, iridium, and alloys thereof. The conductive material may take the form of a continuous sheet or it may be formed from one or more wires, a mesh, a coil, or a braid.

The return electrode 110 may be secured to the desired patient tissue by a variety of techniques. By way of example, the return electrode can be secured to tissue using a temporary, biocompatible adhesive. Alternatively, it can be secured using compression, sutures, clamps or clips, or other mechanical fasteners. Examples of suitable adhesives include hydrocolloid adhesives (available from 3M) and other pressure sensitive adhesives.

In another embodiment, the return electrode may be attached to or integrally formed with another device that is used during the applicable surgical procedure. In the case of heart surgery and procedures involving the ablation of heart tissue (either open chest or thoracoscopic), various positioning devices are utilized to manipulate, move, and reposition the heart during the procedure. Such devices, e.g., heart lifters and positioners, may have attached to a heart contacting surface thereof one or more return electrodes. Alternatively, the return electrode(s) can be integrally formed with such devices. A return electrode design of this type offers the advantage of enabling a surgeon to spatially manipulate the heart with the same device that serves as the return electrode. This ensures good contact of the return electrode with the heart, and the return-electrode can be positioned at any desired location on the heart.

Figure 4:
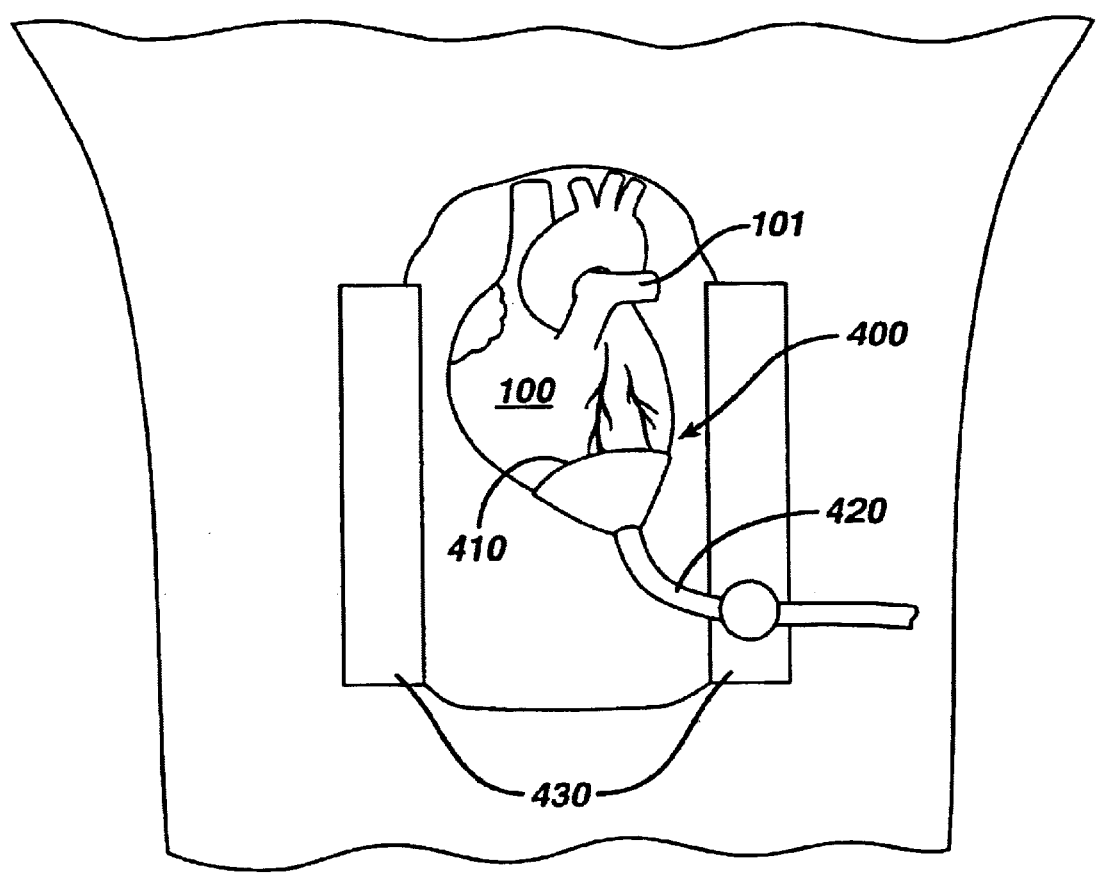
FIG. 4 is a plane view of a the system of the invention utilizing a heart-postioning device as a retune electrode.

FIG. 4 illustrates one example of a heart manipulating device that also includes a return electrode. The apical lifter 400 shown in FIG. 4 includes a return electrode 410 that is formed on a tissue contacting surface of the apical lifter 400. The return electrode 410 may be integrally formed with the apical lifter, or it may be attached to the inner surface of an existing apical lifter. Further, the return electrode may be circumferentially formed within the inner surface of the apical lifter, it may be in the form of one or more strips disposed with the apical lifter, or it may be a conductive element that occupies all or part of the inner surface of the apical member. The return electrode 410 communicates with an energy source (not shown) through a conductor 420.

FIG. 4 shows an apical lifter modified to include a return electrode used in conjunction with open chest surgery wherein retractor blades 430 help to maintain access to the surgical site. In the illustrated embodiment, the apical lifter 400 is secured to the apex of the heart. A variety of techniques can be used to secure such a device to the heart, including compression, suction, biocompatible adhesives (including hydrocolloid adhesives), sutures, clamps or clips and other mechanical fasteners.

Such a device may also be used during a thoracoscopic procedure by providing, for example, an apical lifter or another type of heart manipulating device that is of a first size and shape sufficient to enter a patient's body through a thoracoscopic portal before deployment and a second size and shape following deployment in the body. One of ordinary skill in the art will readily appreciate that the size and shape of such a device may be altered by various techniques, such as by inflation following deployment and/or the use of a shape memory material. Apical lifter 400 may use suction to adhere to apex 440 of heart 100 in order to effect spatial manipulation of heart 100.

Although an apical lifter is the only illustrated example of a heart manipulating device modified to be or include a return electrode, one of ordinary skill in the art will readily appreciate that a variety of other tools and devices may be so modified or constructed according to the principles described above.

One of the ordinary skill in the art will appreciate that any return electrode according to the present invention, not just one associated with a heart manipulating device, may be constructed to enlarge upon deployment within a patient's body. That is, the return electrode may have a first, smaller size and shape before deployment to facilitate easy access to the surgical site, and a second, larger size and shape after deployment within the patient's body. Such a construction can be achieved by the use of a selectively inflatable return electrode, or one that is constructed of a shape memory material.

One of ordinary skill in the art will appreciate that a variety of electrosurgical generators can be used as the energy source 11. In one embodiment, the energy source is a radiofrequency (RF) generator that can operate in bipolar and/or monopolar mode. Such a generator should be capable of delivering RF energy having from about 1 to 100 watts of power and a frequency in the range of about 1 KHz to 1 MHz. More preferably, however, the desired frequency is in the range of about 250 KHz to 600 KHz, and the desired wattage is in the range of about 10 to 50 watts. One example of a suitable energy source is the Pegasys bipolar generator, available from Ethicon Endo-Surgery. Typically, the lesions are formed by delivering the energy for a duration of about 2 to 40 seconds at a power of about 20 to 40 watts.

As noted above, the invention enables an essentially monopolar system to be used in a manner that minimizes the risk of collateral damage by stray current to sensitive tissue structures and organs (e.g., the lungs and esophagus) during an ablation procedure. However, the system may be used with a monopolar and/or bipolar generator system. Although the system utilizes a return electrode that is remote from the energy-delivering electrode, the return electrode is positioned within and in contact with organs or other tissue structures within the patient's body cavity. Preferably, the return electrode is in contact with cardiac tissue.

In one embodiment, the system is useful for ablation of tissue, such as cardiac tissue. In conducting such a procedure, the target tissue is surgically accessed in an appropriate manner (e.g., by open chest surgery or by a thoracoscopic approach) and the return electrode 110 is attached to tissue within the patient's body, in proximity to the target tissue. Preferably, the return electrode is attached to a portion of the heart or other cardiac tissue such as the pericardium, and it is secured to tissue so that the conductive surface area of the return electrode remains in contact with the tissue during the ablation procedure. The energy-delivering electrode 120 is then positioned proximal to, and preferably in contact with, the target tissue to be ablated. As shown in FIG. 1, the energy-delivering electrode 120 is placed on an epicardial surface of the heart, at a location close to a juncture (or ostium) with pulmonary vein 101. This location, within the left atrium of heart 100, is known to be a common atrial fibrillation (AF) focus, ablation of which is effective to block the electrical conduction responsible for the atrial fibrillation. Upon activation of the energy source, current is delivered to the tissue, between the energy-delivering electrode and the return electrodes 120, 100. The current is delivered for a duration of time and at a magnitude sufficient to form a fully transmural (i.e., completely through the heart wall) lesion which will disrupt the AF focus by blocking electrical conduction therein. As noted above, the current may be delivered at a power level of about 20–40 watts for about 2 to 40 seconds. The positioning of the electrodes as described above prevents the conductive pathways through which energy will travel from leaving the heart, thus minimizing the risk of collateral tissue damage by stray current. Use of a small active electrode produces sufficient current density to achieve ablation of tissue in proximity to the active electrode while ensuring that no other damage is done.

FIG. 2 illustrates likely return current paths (I) when the energy-delivering electrode 120 ablates tissue on the epicardial surface of the left atrium 20 with the return electrode attached to an epicardial surface of the right ventricle. As shown, return current paths (I) avoid current- or heat-sensitive structures such as the esophagus 21, spine 22, and lung 23 and tend to be confined to cardiac tissue located between the two electrodes. In this way, the return current paths(I) are less likely to cause collateral tissue damage.

As noted above, embodiments of the system described above may be used by surgeons accessing a patient's body through open chest surgery or by a thoracoscopic approach. Accordingly, type and size of the electrodes, and the method of attachment of return electrode may vary depending upon the requirements of a given application.

One of ordinary skill in the art will appreciate further features and advantages of the invention based on the above-described embodiments. Accordingly, the invention is not to be limited by what has been particularly shown arid described, except as indicated by the appended claims. All publications and references cited herein are expressly incorporated herein by reference in their entity.

What is claimed is:

1. A method of forming a lesion at a predetermined heart location, comprising:
   providing an energy-delivering electrode;
   providing a separate return electrode having a surface area larger than a surface area of the energy-delivering electrode;
   positioning the energy-delivering electrode in contact with a first, cardiac tissue surface at the predetermined heart location;
   positioning the return electrode in contact with a second, cardiac tissue surface at a location remote from the energy-delivering electrode; and
   establishing an electrosurgical current capable of delivering energy through the energy-delivering electrode at the first tissue surface to the return electrode at the second tissue surface at a magnitude and for a duration effective to form a transmural lesion between the first and second tissue surfaces at the predetermined heart location.

2. The method according to claim 1, wherein the electrosurgical current is established by an RF generator.

3. The method according to claim 1, wherein the predetermined heart location is a surface segment of a left atrium.

4. The method according to claim 3, wherein the surface segment is adjacent to a pulmonary vein ostium.

5. The method according to claim 1, wherein the energy-delivering electrode is positioned one of an epicardial heart surface or an endocardial heart surface.

6. The method according to claim 1, wherein the return electrode is positioned in contact with one of atrial tissue, ventricular tissue, a heart apex, and pericardial tissue.

7. The method according to claim 1, wherein the method is performed in conjunction with one of open chest heart surgery and thoracoscopic heart surgery.

8. The method according to claim 7, wherein the method is performed upon a beating heart.

9. The method according to claim 7, wherein the method is performed upon a stopped heart.

10. The method according to claim 1, wherein the return electrode is disposed on a heart-positioning device.

11. The method according to claim 1, wherein positioning the return electrode further comprises:
    maintaining the return electrode in contact with cardiac tissue by use of one of adhesive, suture, clip, clamp, fastener, suction, compression and combinations thereof.

12. A system for treating atrial fibrillation in a heart of a patient by forming a transmural lesion at a predetermined heart location, comprising:
    an energy-delivering electrode adapted to communicate with an energy source; and
    a heart-positioning device effective to grasp and spatially manipulate the heart, the heart-positioning device having a body portion and at least one return electrode disposed on a heart-contacting surface of the body portion, the return electrode having a surface area larger than a surface area of the energy-delivering electrode, the system being capable of selectively establishing an electrosurgical current at the predetermined heart location of a magnitude and for a duration effective in forming the transmural lesion when the electrodes are placed in communication with the energy source.

13. The system according to claim 12, wherein the predetermined heart location is a surface segment of a left atrium.

14. The system according to claim 13, wherein the surface segment is adjacent to a pulmonary vein ostium.

15. The system according to claim 12, wherein the heart-positioning device includes a heart-contacting surface that is selectively coupled to a surface of the heart by use of one of adhesive, suture, clip, clamp, fastener, suction, compression and combinations thereof.

16. The system according to claim 13, wherein the return electrode is integrally formed on a heart-contacting surface of the heart-positioning device.

17. A system for treating atrial fibrillation in a heart of a patient by forming a transmural lesion at a predetermined heart location, comprising:
    an energy-delivering electrode adapted to communicate with an energy source; and
    a heart-positioning device effective to spatially manipulate the heart, having a body portion and at least one return electrode disposed on a heart-contacting surface of the body portion, wherein the heart-positioning device has a first size and shape prior to deployment and a second, larger size and shape following deployment, the system being capable of selectively establishing an electrosurgical current at the predetermined heart location of a magnitude and for a duration effective in forming the transmural lesion when the electrodes are placed in communication with the energy source.

* * * * *